United States Patent [19]

Selkowitz

[11] Patent Number: 4,915,500
[45] Date of Patent: Apr. 10, 1990

[54] MULTICHANNEL OPTICAL SENSING DEVICE

[75] Inventor: Stephen E. Selkowitz, Piedmont, Calif.

[73] Assignee: The United States of America as represented by the Department of Energy, Washington, D.C.

[21] Appl. No.: 766,168

[22] Filed: Aug. 16, 1985

[51] Int. Cl.$^4$ .............................................. G01J 1/42
[52] U.S. Cl. ..................................... 356/221; 356/236
[58] Field of Search ............... 356/121, 213, 218, 221, 356/229, 236, 340, 446

[56] References Cited

U.S. PATENT DOCUMENTS

| | | | |
|---|---|---|---|
| 3,549,264 | 12/1970 | Christie | 356/446 |
| 3,838,926 | 10/1974 | Kato et al. | 356/236 |
| 3,869,208 | 3/1975 | Lorenz | 356/236 |
| 4,102,574 | 7/1978 | Wieder et al. | 356/367 |
| 4,150,898 | 4/1979 | Suga | 356/236 |
| 4,193,691 | 3/1980 | Fjarlie | 356/330 |
| 4,256,405 | 3/1981 | Fjarlie | 356/330 |
| 4,320,969 | 3/1982 | Green | 356/221 |
| 4,395,126 | 7/1983 | Kramer | 356/236 |
| 4,589,732 | 5/1986 | Shiraishi et al. | 350/332 |

Primary Examiner—Richard A. Rosenberger
Attorney, Agent, or Firm—Clifton E. Clouse, Jr.; Roger S. Gaither; William R. Moser

[57] ABSTRACT

A multichannel optical sensing device is disclosed, for measuring the outdoor sky luminance or illuminance or the luminance or illuminance distribution in a room, comprising a plurality of light receptors, an optical shutter matrix including a plurality of liquid crystal optical shutter elements operable by electrical control signals between light transmitting and light stopping conditions, fiber optic elements connected between the receptors and the shutter elements, a microprocessor based programmable control unit for selectively supplying control signals to the optical shutter elements in a programmable sequence, a photodetector including an optical integrating spherical chamber having an input port for receiving the light from the shutter matrix and at least one detector element in the spherical chamber for producing output signals corresponding to the light, and output units for utilizing the output signals including a storage unit having a control connection to the microprocessor based programmable control unit for storing the output signals under the sequence control of the programmable control unit.

9 Claims, 2 Drawing Sheets

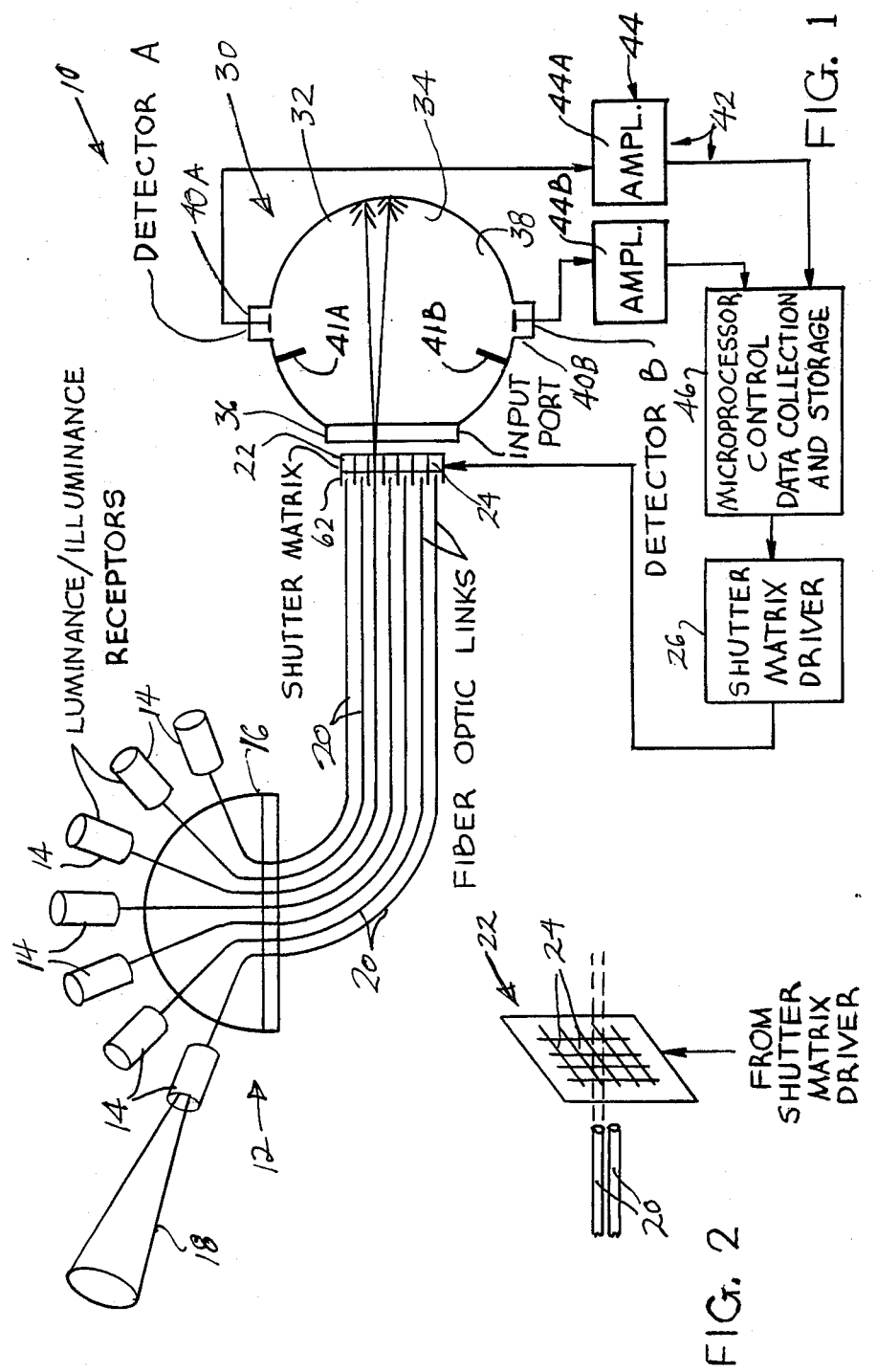

MULTICHANNEL OPTICAL SENSING DEVICE

The United States Government has rights in this invention pursuant to Contract No. DE-AC03-76SF00098 between the United States Department of Energy and the University of California.

FIELD OF THE INVENTION

This invention relates to a multichannel optical sensing device for measuring the distribution of outdoor sky luminance or illuminance, or the distribution of luminance or illuminance in a room or in a scale model of a room, or for any application in which illuminance/luminance data, or radiance/irradiance data, must be gathered efficiently from many discrete locations.

BACKGROUND OF THE INVENTION

It is frequently necessary to measure illuminance or luminance at a number of different locations within a relatively short time period. This applies to both outdoor measurements and indoor measurements in a room. For example, in order to characterize sky luminance distribution, it is desirable to be able to measure the luminance across the sky vault at approximately one hundred locations or directions within a relatively short time interval to insure that the luminance distribution has not changed appreciably during the measurement period. In order to study lighting quality within an architectural space or a scale model of the space, it will often be desirable to measure the luminance of interior room surfaces when the room is lit by electric lighting only, by day lighting only, or with a combination of electric light and day light. Data on luminance distribution within the room is essential in order to calculate the glare index or some other measure of glare or visual comfort.

In other applications it may be desirable to measure the illuminance at many different locations within a building or within a scale model of a building. Each of these applications and other similar photometric or radiometric measurement applications have several requirements in common. They require: (1) relatively high absolute accuracy; (2) high precision in the measurement between channels; (3) minimum calibration drift over time; (4) ability to add or modify input channels; (5) the ability to collect data rapidly from a large number of channels; (6) the ability to transfer the collected data to an accessible file or storage device; (7) the ability to accept luminance and illuminance inputs; and (8) instrumentation which is rugged, durable and requires a minimum of maintenance and care. Low power consumption is also preferable so that, in some applications, the device can be battery-operated over long periods of time.

A number of different approaches have been used for this type of multichannel photometric measurements. One approach is to record a luminance distribution photographically, and then process the photographic record, using a microdensitometer to extract the relevant data. This approach requires a delay between collection of the data and its analysis and also generally suffers from severe calibration problems, since the relationship between film preparation and film development processes may vary with time and with the film production batch. Any single photographic frame will normally be limited to a hemispherical field of view.

The photographic approach can be modified by replacing the film with a video system which allows luminance at each location to be measured and automatically filed as an analog or digital signal in an electronic data bank, optical disc or in magnetic storage. The usefulness of this approach is limited by problems with linearity over a wide dynamic range, calibration, limited field of view, and the cost and complexity of the system.

Another technique is the use of a scanning photometer or radiometer. In this approach, a photometric sensor is mounted on a platform that mechanically scans over the desired field of view. Such systems have traditionally been used for measurements of sky luminance distribution. The scanning approach may also utilize a fixed photometric sensor with a scanning mirror system to send the light to the photometer. In either case, the mechanical requirements for a precision scanning device tend to make such approaches costly. The mechanical operation may also set a minimum scan time which may increase the total required time interval for a full scan sequence.

Still another approach is to design a device around an array of sensors, each of which operates independently, but all of which feed data to the same central unit. This approach will tend to produce a bulky unit if many sensors are required and will certainly be expensive, given the cost of high quality photometric sensors. In addition, due to the large number of individual sensors used, calibration between sensors becomes an important problem.

SUMMARY OF THE INVENTION

Considering this background, one principal object of the present invention is to provide a new and improved multichannel optical scanning device which overcomes most of the limitations and problems associated with the prior devices, while providing an improved solution to the problem of rapidly and accurately measuring the distribution of luminance and illuminance, both outdoors and indoors, and at remarkably low cost.

A further object is to provide a new and improved multichannel optical scanning device which is also applicable to the measurement of radiance and irradiance, either with a wide spectral band, or with any narrow spectral band for specific applications.

It will be understood that whenever measurements of luminance and illuminance are referred to herein, measurements of radiance and irradiance are also contemplated. When light is referred to herein, radiation is also contemplated, outside the visible spectrum.

To accomplish these and other objects, the present invention provides a multichannel optical sensing device, comprising a plurality of light receiving elements or receptors for receiving light from various directions, an optical shutter matrix including a plurality of optical shutter elements operable by electrical control signals between light transmitting and light stopping conditions, a plurality of fiber optic elements connected between the light receptors and the optical shutter elements of the matrix, shutter control means for selectively supplying electrical control signals to the optical shutter elements for selectively switching such elements to the light transmitting condition, a photodetector device for receiving the light from all of the optical shutter elements of the matrix, such photodetector device including detector means for producing electrical output signals corresponding to the received light, and output means for utilizing the output signals from the detector means.

A multitude of light receptors may be employed and may be aimed in a large number of different directions to cover a wide distribution. The receptors may include filters, diffusers and various other light control elements, such as cylindrical shields for regulating the acceptance angle of the receptors.

The fiber optic elements are flexible so that the sensors can be aimed in any direction. The fiber optic elements act as light pipes to carry the light from the receptors to the shutter matrix. All of the fiber optic elements are normally the same in length and size to minimize calibration problems but could vary widely in length and size for special purpose applications.

The optical shutter matrix preferably employs liquid crystal devices as the optical shutter elements. Such liquid crystal devices can be switched electronically very rapidly between the light transmitting and the light stopping conditions.

The control unit for the optical shutter matrix is preferably programmable and preferably utilizes a programmable microprocessor, so that the sequence control is derived from software. In this way, the sequence control can be modified, as desired, by changing the software. The optical shutter elements can be activated individually or in any desired combination, on the basis of any desired sequence.

The photodetector device preferably comprises an optical integrating sphere, including a generally spherical integrating chamber having an input port for receiving the light from all of the optical shutter elements. At least one detector element is provided in the spherical integrating chamber for producing output electrical signals corresponding to the received light. Two or more detector elements may be provided in the spherical integrating chamber, in which case the detector elements may have different spectral or other calibration characteristics, for example to provide adequate sensitivity over a wider range of signals.

An amplifier or amplifiers may be provided to amplify the output signals from the detector element or elements. If there are two or more detector elements, the amplifiers may combine the output signals from the detector elements, or may amplify them separately for subsequent processing and summation. The output means may comprise digitizing means for digitizing the output signals, and calibration means for modifying the output signals in accordance with any desired calibration curve or curves. Other signal processing means may also be employed.

The output means may preferably include storage means for storing the output signals from the photodetector device. The storage means preferably has a control connection to the programmable control unit, so that the output signals or data are stored under the sequence control of the programmable control unit. In this way, the storage of the output data is coordinated with the operating sequence of the shutter matrix.

The data may be analyzed in real time as collected, and the subsequent programmable control sequence may be altered, based upon the results of the real time data analysis.

The output means may also comprise a data display device, for displaying the output data, and some other output device, such as a printer.

BRIEF DESCRIPTION OF THE DRAWINGS

Further objects, advantages and features of the present invention will appear from the following description, taken with the accompanying drawings, in which:

FIG. 1 is a diagrammatic illustration of a multichannel optical sensing device, to be described as an illustrative embodiment of the present invention.

FIG. 2 is a fragmentary diagrammatic perspective view, illustrating details of the shutter matrix.

DETAILED DESCRIPTION OF AN ILLUSTRATIVE EMBODIMENT

Figure 3:
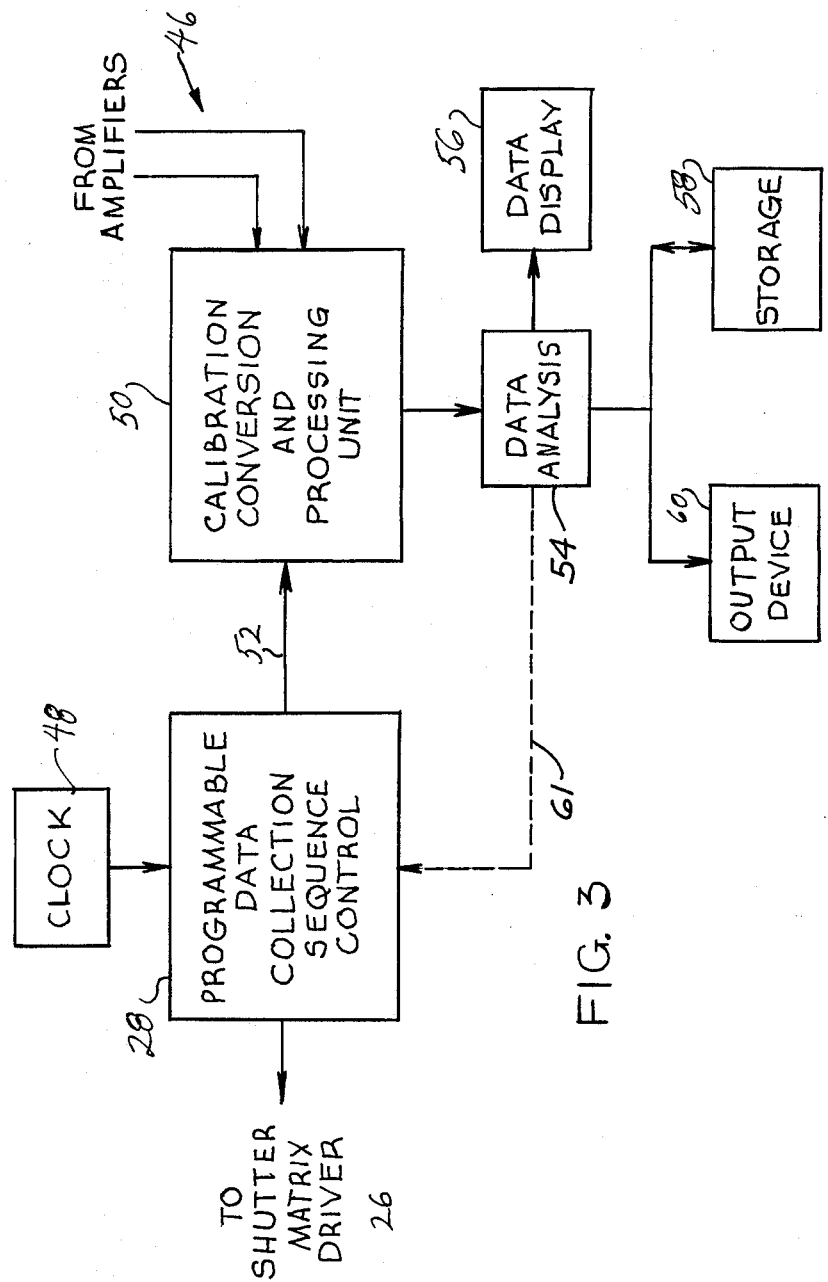
FIG. 3 is a block diagram of the control system and the output system for the multichannel optical sensing device of FIGS. 1 and 2.

As just indicated, FIGS. 1–3 illustrate a multichannel optical sensing device 10 to be described as an illustrative embodiment of the present invention. The multichannel device 10 comprises a multichannel optical receptor array 12, comprising a plurality of optical receptors 14 which may be aimed in various directions. There may be a multitude of the optical receptors 14, such as one hundred or more. The receptors 14 may be supported by a supporting structure 16.

The receptors 14 may be constructed to respond to either the exitance of a distant source or the flux density incident at the receptor locator. Thus, in the case of visible light, either luminance or illuminance can be measured. If desired, the receptors 14 may include various elements for calibration and correction purposes. Thus, the receptors 14 may include filters, diffusers and the like. The receptors 14 are illustrated as being generally cylindrical in shape, but may be any appropriate shape to respond to incident flux, and may be arranged to limit the angle of acceptance of the receptors. For many applications, it is desirable to construct the receptors 14 so that they accept light from a fairly narrow conical angle, such as the conical angle 18, shown in FIG. 1.

The receptors 14 are connected by a corresponding number of fiber optic links 20 to an optical shutter matrix 22, comprising a plurality of optical shutter elements 24, as shown most clearly in FIG. 2, adapted to be switched by electrical control signals between a light stopping condition and a light transmitting condition. Thus, the optical shutter elements 24 are in the form of electrically switchable devices. The optical shutter matrix 22 thus comprises a matrix of electrically switchable devices or cells 24, for receiving the light from the fiber optic links 20, which serve as light pipes to carry the light from the receptors 14. It will be understood that the optical shutter elements 24 may take the form of any known or suitable electrically switchable devices.

The optical shutter elements 24 of the matrix 22 may be activated in any desired sequence or combination by electrical control signals from a shutter matrix driver 26, under the control of a programmable control unit 28, which preferably utilizes a programmable microprocessor having software based programming, affording great flexibility in programming. The control unit 28 may be programmed so that the user may change the operating sequence of the optical shutter elements 24. The control unit 28 may also be programmed so that the operating sequence is determined in part by the results of the prior received data.

The light transmitted by each or all of the optical shutter elements 24 of the matrix 22 is received by a single photodetector device 30, preferably comprising an optical integrating sphere 32 having a generally spherical integrating chamber 34 therein. The light from all of the optical shutter elements 24 of the matrix 22 passes into the spherical chamber 34 through an input port 36 therein. The spherical integrating chamber 34 may have a diffusely reflecting interior surface 38 which is generally spherical in shape. Thus, the interior surface 38 may be white in color with a matte or flat texture.

The spherical integrating chamber 34 has detector means therein, including at least one detector element 40A, for producing electrical output signals corresponding to the light which enters the chamber 34. Preferably, the spherical chamber 34 has at least two detector elements 40A and 40B therein for producing electrical output signals. The detector elements 40A and 40B may be the same, but preferably they have different characteristics, such as different spectral response characteristics, or different dynamic range characteristics, for example. In this way, the output response characteristics of the photodetector device 30 can be changed by modifying the calibration and signal processing circuits which are employed to process the signals from the two detectors 40A and 40B. Detector shields 41A and 41B are preferably provided in the chamber 34 to shield the detectors 40A and 40B from direct radiation from the port 36, so that only reflected radiation reaches the detectors 40A and 40B.

The output signals from the photodetectors 40A and 40B are processed by output means 42, which may comprise amplifier means 44 and a combination output and control unit 46, which is labelled MICROPROCESSOR CONTROL, DATA COLLECTION AND STORAGE in FIG. 1. The amplifier means 44 preferably comprises two amplifiers 44A and 44B which may amplify the two output signals and pass them on separately to the combination output and control unit 46, for separate processing and subsequent combination in a programmable manner.

Further details of the combination output and control unit 46 are illustrated in FIG. 3, which shows that the programmable data collection sequence control unit 28 is a component of the unit 46. Timing pulses for the programmable control unit 28 are supplied by a clock-pulse unit 48. The output signals from the amplifiers 44A and 44B are supplied to a calibration, conversion and processing unit 50, which may include digitizing means, such as an analog-digital convertor for converting the output signals from analog to digital form. The unit 50 may also include calibration means for modifying the output signals in accordance with any desired calibration curve, in accordance with signal processing techniques which are known to those skilled in the art. The signal processing operations of the unit 50 may be synchronized and controlled by means of a control connection 52 between the programmable control unit 28 and the unit 50.

In some cases, the photodetectors 40A and 40B are of the same type, but with different ranges. For example, one detector may be adapted to respond to low level signals, while the other detector is adapted to respond to high level signals. For this detector arrangement, the processing unit 50 is programmed to treat the detector signals separately and to select the appropriate value based upon the appropriate range for the particular signals being processed.

In other cases, the two detectors 40A and 40B may be of different types. For example, one detector may be photometric while the other detector is radiometric. Again, the processing unit 50 is programmed so that the two signals are initially processed separately. The processing unit 50 may advantageously be programmed to compute the ratio of the individual signal values from the two detectors. The ratio values, as well as the individual signal values, may be supplied as output signals, for storage and display, as well as possible further analysis.

The photodetectors 40A and 40B generate electrical signals, such as voltage, corresponding to the light or radiation received by the detectors. The signals must be converted to engineering units, such as lux. Since the detectors 40A and 40B operate over a wide signal range, the detectors have calibration curves representing the relationship, over the wide signal range, between the output electrical signals and the engineering units. Each individual photodetector has its individual calibration curve, depending upon its exact construction. Moreover, the calibration curves are dependent upon environmental variables, such as the prevailing temperature.

The calibration conversion and processing unit 50 performs the calibration functions for the photodetectors 40A and 40B by standard computerized data processing techniques. Thus, the calibration curves for the detectors may be installed in the unit 50 in the form of sets of calibration values, stored in programmable electronic memories, which deliver the output engineering values in response to the input electrical values. This type of a programmable electronic memory is sometimes referred to as an electronic look-up table. Such programmable electronic memories can be programmed to accomplish any desired calibration conversion. The analog signals from the detectors 40A and 40B are digitized by analog-digital convertors, before being supplied to the calibration conversion memories. The programming for the calibration conversion memories is preferably provided by software, for the sake of maximum flexibility, so that the programming can be changed for different applications, by providing appropriate software. The calibration conversion units can also be programmed to correct for changes in environmental conditions, such as the prevailing temperature. This type of calibration conversion is well known to those skilled in the art of computerized data processing, as it relates to scientific data.

The processed signal data from the unit 50 is supplied to a data analysis unit 54, which performs further data processing, such as computation operations. The data from the unit 54 is supplied to a data display unit 56, a storage unit 58, and an output device 60. The data display unit 56 preferably provides a video or other similar display. The storage unit 58 utilizes electronic storage, magnetic storage, or preferably a combination of both, such storage being accessible to the data analysis unit 54. The output device 60 preferably includes various hard copy options, such as a printer, a plotter or the like, for printing or plotting the output data, as desired.

The data analysis unit 54 is programmable to perform a variety of computations. The programming is selected to perform computations which are necessary or appropriate for the specific measurement application. For some applications, the computations include summing and normalizing the data from many channels to obtain an integrated value. For various applications, the computations may involve performing statistical analysis, such as averaging, binning, computing standard deviations, and the like. Some applications call for performing various comparisons, such as all channels from the left quadrant versus all channels from the right quadrant, or a time-based comparison to show which channels are changing most rapidly with time. Various other comparisons can be performed.

The data analysis unit 54 is preferably programmable by standard scientific data processing software, which may be selected and utilized to perform the desired computational, statistical, comparison and other analyses. The data analysis unit 54 is also preferably programmable by error-checking software to determine whether any channel is out of its range and whether the various computations, comparisons and analyses are providing plausible results.

The data analysis unit 54 preferably includes a control output link or connection 61, shown diagrammatically in FIG. 3, so that the data analysis unit 59 has the ability to alter the operation of the programmable data collection sequence control 28, based upon the results of the analyses performed by the data analysis unit 54. The control link or connection 61 is shown as a broken line arrow between the data analysis unit 54 and the programmable data collection sequence control 28, in FIG. 3. Various control modes may be performed by the control link 61, depending upon the programming selected for the data analysis unit 54 and the sequence control 28. One useful control mode is a repeat mode, whereby the data analysis unit 54 causes the sequence control 28 to repeat a particular data collection sequence or scan of the shutter matrix 22, if the results produced by the data analysis unit 54 are not reasonable, for a particular scan, as determined by the error-checking programming of the data analysis unit 54. Another useful control mode is a cycle time control mode, in which the data analysis unit 54 causes the sequence control 28 to change various elements of the cycle timing, such as the open time of each element 24 in the shutter matrix 22, the interval between shutter operations, or the total cycle time for the shutter, in response to various output conditions determined by the data analysis unit 54, such as the intensity of the signals received from the photodetectors 40A and 40B, or the rate of change of such signals. The data analysis unit 54 may store the output data from prior scans and may recall such data from the storage unit 58, for comparison with the output data from later scans, in exercising its control mode over the sequence control 28, to improve the quality of the output data.

As indicated above, the data display unit 56 includes a real time video display which provides not only a glimpse of the data being collected, to confirm proper operations, but also allows the user to inspect all operating files, prior data which has been stored in the storage unit 58, and the channel sequence. The video display is arranged to provide communication to and contact with all elements of the data acquisition, processing and storage system. The processing unit 50, the data analysis unit 54 and the sequence control 28 are preferably programmed to operate the video display and to provide for the display of numerical data, curves, graphs and the like, as selected by the user for specific applications.

The receptors 14 and the fiber optic links 20 form fiber optic probes which can be used to measure luminance or illuminance. The fiber optic links 20 are adapted to channel the desired light signals to the shutter matrix 22 and then to the photodetector device 30. A multitude of the receptors 14 and the fiber optic links 20 can be provided, so that there is no need to impart a physical scanning movement to the receptors 14.

The fiber optic links 20 are generally of short length, typically from six inches to two feet. However, even for a length of 4 to 6 feet, the optical quality of the fiber optic links is generally not a limiting concern. In most cases, it is possible to employ low-cost plastic fiber optics, which will afford acceptable quality for many applications. The array 12 of fiber optic receptors 14 is arranged to collect the desired light signals from the appropriate spatial locations or directions. For example, in the case of the sky luminance measurement system, the desired measurement points are determined, and the fiber optic receptors 14 are mounted in the supporting structure 16 so that the receptors point to each location in the sky at which a measurement is desired. The supporting structure 16 may be arranged to hold the fiber optic receptors 14 in any known or suitable manner. To simplify calibration, all of the fiber optic links 20 should be of the same length and diameter.

The fiber optic probes, formed by the receptors 14 and the fiber optic links 20, may be employed for the measurement of either luminance or illuminance. For the measurement of luminance, the receptors 14 modify the acceptance angle of the fiber optic links or strands 20. For a fiber optic strand with a flat polished end, the cone of acceptance varies depending upon the index of refraction of the optical material in the strand. Most materials collect light from a cone of approximately thirty degrees to fifty degrees, full angle. In many applications, a much narrower field of view is desired for the measurement of luminance. In such cases, the receptors 14 comprise cylindrical collars which are slipped over the ends of the fiber optic links or strands 20. Such collars have sufficient depth so that the field of view of the end of the fiber optic strand is restricted by the depth of the cylindrical collar. For precision measurements, the collar is painted black inside and has longitudinal light baffles or partitions to prevent stray light from being reflected obliquely from the inside walls of the collars. Thus, stray light is prevented from reaching the end of the fiber optic strand 20.

For the measurement of hemispherical illuminance, the receptors 14 are of the conventional cosine corrected construction, in which each receptor includes a cosine-corrected diffuser, through which the light must pass to reach the end of the corresponding fiber optic strand 20. Receptors of this construction, for the measurement of illuminance, have the advantage of being very small in size. Appropriate receptors for cylindrical or spherical illuminance or any other special purpose illuminance measurement can be readily constructed in a similar manner.

The output ends of the fiber optic links 20 are suitably supported, as by a holder 62, so that the output ends of the fiber optic links 20 are aligned with the individual optical shutter elements 24 of the shutter matrix 22. The matrix 22 is constructed so as to obviate any substantial cross-talk between the adjacent optical shutter elements 24.

In order to facilitate making different types of measurements, it is advantageous to provide a plurality of different receptor arrays 12 and associated fiber optic links 20, which can be plugged in to the shutter matrix 22, interchangeably.

The electrically operable shutter matrix 22 preferably employs liquid crystal devices as the individual optical shutter elements 24. However, other electrically operable optical shutter devices may be employed, such as devices utilizing electrochromic optical switching films. Liquid crystal shutter devices have many advantages, in that they provide relatively fast switching time. Moreover, they are highly transparent and highly reflective in their oppositely switched states. Moreover, the provision of liquid crystal shutter cells makes it possible to fabricate the shutter matrix with relatively small individual shutter cells or elements. Furthermore, liquid crystal shutter elements provide substantially uniform spectral transmissivity across the spectral range of interest. They also provide a minimal change in shutter switching characteristics over long cycle times, and are reasonable in cost.

The shutter matrix 22 may have a moderate to large number of discrete switchable shutter elements 24. The shutter matrix 22 may be square or circular in the shape of its pattern, or may be of some other shape, such as linear. If it is desired to modify the spectral transmission characteristics of the shutter elements 24, a suitable filter may be employed between the shutter matrix 22 and the input port 36 of the photodetector device 30.

Since the optical shutter elements 24 are independently controlled, the shutter matrix 22 provides great versatility, in that the matrix has the ability to transmit single channels in any sequence, or multiple channels in any combination.

It is highly advantageous to provide a programmable microprocessor based control unit 46 for controlling the optical shutter elements 24, because the time sequencing of the data collection can be controlled by software programming, subject only to the limitation of the maximum shutter speed. The sequencing can be modified, as desired, by changing the software programming. Moreover, the signal processing can be modified by changing the software programming. Thus, different software programming can be provided for various different measurement operations. For example, if a symmetrical luminance distribution is to be measured, the symmetrical spatial areas can be directly compared, with appropriate software programming, by comparing the output signals from those particular receptors. Little or no signal conditioning or data manipulation is required for this purpose. Different software programming may be provided for other measurement operations.

It is possible to provide a high degree of spatial resolution by providing a large number of receptors 14, fiber optic links 20, and optical shutter elements 24.

Testing the multichannel optical sensing device 10 for calibration can readily be accomplished by placing the receptor array 12 in an environment having a known distribution of luminance or illuminance, and then testing the output from each receptor channel individually and adding all channels to be sure that the integrated luminance measurement is equal to the measured illuminance.

The optical shutter matrix 22, with its programmable control unit 28, provides unique possibilities of measurement sophistication and versatility, which are believed to constitute a significant improvement over prior measurement systems.

The photodetector device 30, utilizing the optical integrating sphere 32, has the important advantage that the light signals from all of the optical shutter elements 24 are passed into the spherical integrating chamber 34 and are detected by the same photodetector element or elements 40A and 40B. Thus, the light signals from all of the receptors 14 are detected by the same photodetector element or elements. Thus, there is no problem of comparative calibration between the various receptors 14. The calibration for the signals from all of the receptors 14 is the same.

While a single photodetector element 40A can be employed in the integrating spherical chamber 34, it is often more advantageous to provide two or more photodetector elements, as represented by the elements 40A and 40B of FIG. 1. The detector elements may have different intensity responses as well as different wavelength responses, in the same integrating sphere. The different response characteristics make it possible to perform comparative radiometric and photometric measurements at the same time. Moreover, by providing photodetector elements having different dynamic range characteristics, it is possible to make better measurements over a broader dynamic range, without exceeding the limits of a single photodetector element.

The photodetector elements 40A and 40B are preferably silicon photodiodes which generate signals corresponding to the received light.

Rather than utilizing a photodetector device having an optical integrating sphere, it is possible to use some other type of photodetector device capable of receiving the light from all of the optical shutter elements 24. For example, a large silicon photodiode may be employed, large enough to receive the light from all of the shutter elements 24. However, such a large silicon photodiode generally suffers from the disadvantage of requiring comparative calibration between the various receptor channels, because the light from each sensor channel falls upon a different portion of the photodetector diode.

It is highly advantageous to operate the optical shutter elements 24 under the control of the microprocessor based programmable control unit 28, because the programmable control unit 28 makes it possible to activate or open the optical shutter elements 24 in any desired sequence, either individually or in any desired combination or combinations. The microprocessor based programmable control unit 28 preferably utilizes software programming, so that the operating sequence of the optical shutter elements 24 can be changed very readily, by providing modified software programming. Various programming discs or other software may be provided for different measurement operations, as needed.

The software based programmable control unit 28 controls all aspects of the operation of the optical shutter elements 24, including not only the sequence of operation, but also the cycle time, the repetition rate, and the time allocated to the opening and closing of each of the optical shutter elements 24.

It is also highly advantageous to employ the software based programmable control unit 28 to control the operation of the output system 46, so that such operation will be synchronized and coordinated with the operation of the optical shutter elements 24. Thus, the software based programmable control unit 28 is advantageously employed to control the digital conversion, calibration and signal processing operations of the unit 50, the data analysis operations of the unit 54, the data display operations of the unit 56, the data storage operations of the unit 58, and the printing or other operations of the output device 60. All of these operations may be controlled differently for different measurement operations, by providing appropriate software programming.

The calibration conversion and processing unit 50, the data analysis unit 54, the data display unit 56, the storage unit 58, and the programmable data collection sequence control 28 are all preferably provided by any standard minicomputer or microcomputer, having adequate memory, software programming, magnetic disc storage, and a video display. As to software programming, both standard programming and custom programming are preferably employed. The production of the custom programming is within the skill of the art in computer programming.

The shutter matrix driver 26 takes the form of a multichannel amplifier for driving all of the shutter elements 24 of the shutter elements 24 of the shutter matrix 22.

The detector shields 41A and 41B are preferably in the form of baffles within the spherical integrating chamber 34 of the optical integrating sphere 32, to intercept and prevent the direct transmission of light or radiation between the input port 36 and the photodetectors 40A and 40B. The shields 41A and 41B project inwardly from the spherical inner surface 38 of the integrating sphere 32 and are located between the input port 36 and the photodetectors 40A and 40B, as shown in FIG. 1.

When the word radiation is used herein, it is intended to include visible light, ultraviolet radiation, infrared radiation and other forms of radiation. The word optical is intended to contemplate the handling of both light and radiation.

Various modifications, alternative constructions and equivalents may be employed, within the true spirit and scope of the present invention, as described herein and defined in the following claims.

I claim:

1. A compact multichannel optical sensing system for measuring the outdoor sky luminance or illuminance or the luminance or illuminance in a room by sampling in multiple directions, comprising a plurality of light receptors for receiving light separately and independently from various directions for transmission therethrough, each of said receptors being mounted so as to be directed to receive light along different diverging angles with respect to each other, an optical shutter matrix including a plurality of optical shutter elements operable by electrical control signals between light transmitting and light stopping conditions, a plurality of fiber optic elements connected between said light receptors and said optical shutter elements, shutter control means for selectively supplying one or more electrical control signals to said optical shutter elements, said shutter control means comprising a programmable control unit for controlling the sequence or combination with which the electrical control signals are supplied to said optical shutter elements, a photodetector device for receiving all of the light transmitted from said receptors and fiber optic elements by said optical shutter matrix, said photodetector device including an optical integrating sphere having a generally spherical integrating chamber with an input port for admitting the light selected under control of said control means to pass from said matrix into said spherical chamber, said spherical chamber having detector means therein for producing electrical output signals corresponding to the light received by said spherical chamber, and output means for utilizing said output signals for analysis of the luminance or illuminance.

2. A multichannel optical sensing device according to claim 1,
in which said optical shutter elements comprise liquid crystal devices.

3. A multichannel optical sensing device according to claim 1,
in which said programmable control unit comprises a programmable microprocessor.

4. A multichannel optical sensing device according to claim 3,
including a shutter matrix driver connected between said programmable control unit and said optical shutter elements of said matrix.

5. A multichannel optical sensing device according to claim 1,
said detector means comprising at least two detector elements in said spherical chamber for producing output signals corresponding to the light received by said chamber,
said output means including amplifiers for amplifying the output signals from said detector elements.

6. A multichannel optical sensing device according to claim 1,
said output means including storage means for storing the output signals from said detector means,
said storage means having a control connection to said programmable control unit for storing said output signals under the sequence control of said programmable control unit.

7. A multichannel optical sensing device according to claim 1,
said output means including calibration means for modifying said output signals to calibrate said detector element.

8. A multichannel optical sensing device according to claim 1,
said output means including digitizing means for digitizing said output signals.

9. A multichannel optical sensing device according to claim 1,
in which said optical integrating sphere includes a detector shield in said chamber for intercepting direct transmission of radiation between said input port and said detector element.

* * * * *